US006839439B2

(12) United States Patent
Daly

(10) Patent No.: US 6,839,439 B2
(45) Date of Patent: Jan. 4, 2005

(54) METHOD AND APPARATUS FOR ACTIVE NOISE CONTROL IN AN AIR INDUCTION SYSTEM

(75) Inventor: Paul D. Daly, Troy, MI (US)

(73) Assignee: Siemens VDO Automotive Inc., Chatham (CA)

(*) Notice: Subject to any disclaimer, the term of this patent is extended or adjusted under 35 U.S.C. 154(b) by 174 days.

(21) Appl. No.: 10/355,656

(22) Filed: Jan. 31, 2003

(65) Prior Publication Data

US 2003/0152238 A1 Aug. 14, 2003

Related U.S. Application Data

(60) Provisional application No. 60/357,998, filed on Feb. 14, 2002.

(51) Int. Cl.[7] ........................ A61F 11/06; G10K 11/16; H03B 29/00

(52) U.S. Cl. ..................... 381/71.5; 381/71.7; 181/224

(58) Field of Search .............................. 381/71.5, 71.3, 381/71.7, 71.8, 71.9; 181/224, 206, 214; 95/18, 29, 60

(56) References Cited

U.S. PATENT DOCUMENTS 5,336,856 A * 8/1994 Krider et al. ............... 181/206
5,694,477 A * 12/1997 Kole .......................... 381/111
5,717,774 A * 2/1998 Kole .......................... 381/111
6,084,971 A 7/2000 McLean
6,605,131 B2 * 8/2003 Vanderveen et al. ........... 95/11
6,625,285 B1 * 9/2003 Ohashi ...................... 381/71.3
6,684,977 B2 * 2/2004 Stuart ......................... 181/206
2004/0170287 A1 * 9/2004 Biwa et al. ................ 381/71.5

FOREIGN PATENT DOCUMENTS

JP 05173578 * 7/1993 ................ 381/71.5

* cited by examiner

*Primary Examiner*—Xu Mei

(57) ABSTRACT

An air induction system for an internal combustion engine utilizes localized heat generation to produce a desired acoustic profile that attenuates noise propagated through the air induction system. The noise propagated through the air induction system varies over time to form a variable noise profile. A heat generating mechanism, such as a laser array or electric spark generator, produces a predetermined amount of heat within a localized area adjacent to an inlet to the air duct housing. The predetermined amount of heat is an amount of heat sufficient to produce a desired acoustic energy as a result of rapid air expansion at the localized area. A controller varies the predetermined amount of heat over time to produce a desired acoustic profile that cancels the variable noise profile.

20 Claims, 2 Drawing Sheets

METHOD AND APPARATUS FOR ACTIVE NOISE CONTROL IN AN AIR INDUCTION SYSTEM

CROSS-REFERENCE TO RELATED APPLICATIONS

The application claims priority to U.S. Provisional Application No. 60/357,998, which was filed on Feb. 14, 2002.

BACKGROUND OF THE INVENTION

This invention relates to a method and apparatus that uses localized heat generation to produce a desired acoustic profile to attenuate noise propagated through an air induction system.

An internal combustion engine utilizes an air induction system to conduct air to engine cylinders. Engine noise is propagated through the air induction system, which is undesirable. Noise attenuation mechanisms have been installed within the air induction system to reduce these noises. A typical feed forward noise attenuation mechanism includes a loudspeaker, a microphone, and a signal generator/computer, which are mounted within an air inlet duct housing. The microphone detects the noise error and generates a noise error signal that is sent to the signal generator/computer. The signal generator/computer creates a corrected phase-shifted signal and sends that back to the speaker to generate a sound field that cancels out the noise that is being detected by the microphone.

While these systems can operate effectively to reduce noise, there are some disadvantages with the loudspeaker noise attenuation mechanism. One disadvantage is that a significant number of components, with associated electrical connections, are required to operate the mechanism, which increases cost and assembly time. Another disadvantage is that large speaker sizes are required to reduce engine noise levels below accepted values. Typically, engine noise must be reduced below 110 Hertz (Hz). This causes the noise attenuation mechanism to be very large, since speaker effectiveness is less at lower frequencies, taking up a considerable amount of packaging space. Additionally, these noise attenuation mechanisms draw a large amount of power from the vehicle electrical system in order to effectively cancel the high levels of low frequency noise.

Thus, it is desirable to have a method and apparatus that can reduce noise as well or better than traditional noise attenuation mechanism but operates more efficiently and effectively, with fewer components, as well as overcoming the other above mentioned deficiencies with the prior art.

SUMMARY OF THE INVENTION

An air induction system for an internal combustion engine utilizes localized heat generation to produce a desired acoustic profile that attenuates or cancels engine noise propagated through an air duct housing. The engine noise varies over time to form a variable noise profile. A heat generating mechanism produces a predetermined amount of heat within a localized area adjacent to an inlet to the air duct housing. The predetermined amount of heat is an amount of heat sufficient to produce a desired acoustic energy as a result of rapid air expansion at the localized area. A controller varies the predetermined amount of heat over time to produce a desired acoustic profile that cancels the variable noise profile.

The system preferably includes a sound detector that senses the noise emanating from the air duct housing and generates a noise signal corresponding to the noise. The signal in response to the noise signal to produce the desired acoustic profile as a phase-shifted acoustic profile that cancels the variable noise profile.

In one disclosed embodiment, the heat generating mechanism comprises an electrical spark generator that produces a plurality of electrical sparks within the localized area to form the phase-shifted acoustic profile. The electrical sparks rapidly heat a very small area of air, resulting in rapid air expansion, which generates a corresponding amount of acoustic energy. By controlling number of sparks produced and the magnitude of each spark over time, a desired acoustic profile can be generated.

In one disclosed embodiment, the heat generating mechanism comprises a plurality of lasers. The lasers are arranged in an array and produce a plurality of laser beams that are directed toward a curved surface mounted within the inlet of the air duct housing. The curved surface reflects each of the beams to a common focal point, i.e. the localized area. This causes a high concentration of heat at a small area, resulting in rapid air expansion, which generates a corresponding amount of acoustic energy. By controlling which lasers are activated, alone or in combination, and by controlling the duration of time each laser is active, a desired acoustic profile can be generated.

The subject system and method provides a simple and effective method for active noise cancellation that eliminates the need for a loudspeaker system, thus reducing the amount of packaging space required for an active noise cancellation system. These and other features of the present invention can be best understood from the following specifications and drawings, the following of which is a brief description.

DETAILED DESCRIPTION OF A PREFERRED EMBODIMENT

Figure 1:
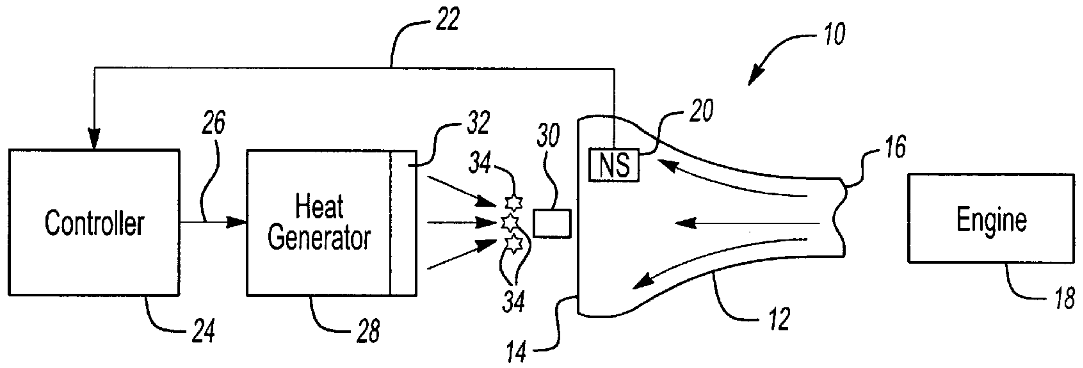
FIG. 1 is a schematic diagram of an air induction system with a noise attenuation system incorporating the subject invention.

An air induction system incorporating the subject active noise attenuation system is shown generally at 10 in FIG. 1. The air induction system 10 includes an air duct housing 12 having an inlet 14 and an outlet 16 operably connected to an engine 18. The engine 18 produces noise that is propagated back through the air duct housing 12, as indicated by the arrows.

A noise detector or noise sensor assembly 20 measures the noise, and generates a noise signal 22 that is communicated to a controller 24. The controller 24 generates a control signal 26 that is communicated to a heat generating mechanism 28. The controller 24 activates the heat generating mechanism 28, which utilizes localized heat generation to produce a desired acoustic profile that attenuates or cancels the noise propagated through the air duct housing 12.

The noise varies over time to form a variable noise profile, which is tracked and represented by the noise signal 22. The heat generating mechanism 28 produces a predetermined amount of heat within a localized area 30 adjacent to the inlet 14 to the air duct housing 12. The predetermined amount of heat is an amount of heat sufficient to produce a desired acoustic energy as a result of rapid air expansion at the localized area 30. The controller 24 determines and varies the predetermined amount of heat over time to produce a desired acoustic profile that cancels the variable noise profile.

The heat generating mechanism 28 can be any type of heat generating mechanism known in the art. In the embodiment of FIG. 1, the heat generating mechanism 28 includes an electrical spark generator 32 that produces a plurality of electrical sparks 34 within or near the localized area 30 to form the phase-shifted acoustic profile. The electrical sparks 34 rapidly heat a very small area of air, resulting in rapid air expansion, which generates a corresponding amount of acoustic energy. By controlling number of sparks 34 produced and by controlling the magnitude of each spark 34 over time, a desired acoustic profile can be generated. The controller 24 determines the appropriate number and magnitude of the sparks 34 and controls spark production via the control signal 26. The control signal 26 and the number and magnitude of sparks 34 vary over time in response to the variable noise profile. Thus, as the engine noise changes, the number and/or magnitude of sparking will correspondingly change to actively cancel or attenuate the undesired engine noise. It should be understood that any electrical spark generator 32 known in the art could be used.

Figure 2:
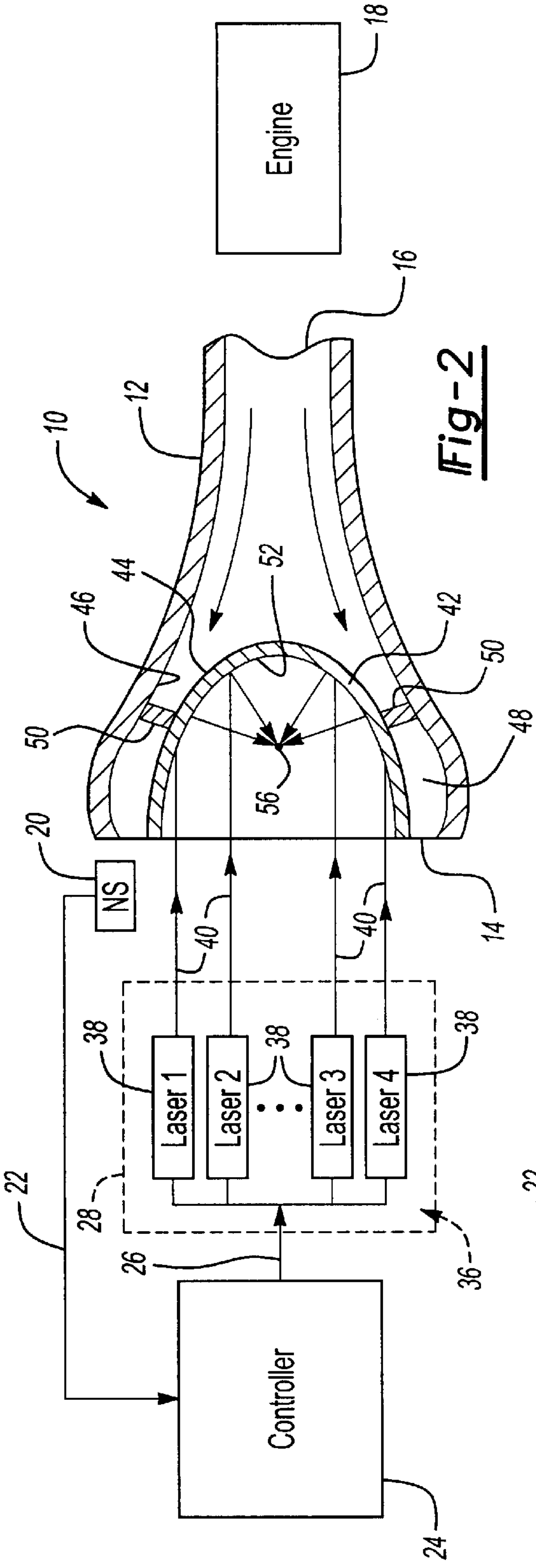
FIG. 2 is a schematic diagram of one embodiment the noise attenuation system.

In the embodiment shown in FIG. 2, the heat generating mechanism 28 comprises a laser array, shown generally at 36. The laser array 36 includes a plurality of lasers 38 that each transmits a laser beam 40 toward a curved surface. Preferably a curved member 42 is mounted within the air duct housing 12 adjacent to the inlet 14. An exterior surface 44 of the curved member 42 is spaced apart from an interior surface 46 of the air duct housing 12 to form an annular passage 48 for air flow. The curved member 42 is preferably attached to the air duct housing 12 with struts 50 or other similar members.

The curved member 42 defines a concave surface 52 that faces the laser array 36. Any type of curved surface profile can be used, such as a parabolic surface, for example. The laser beams 40 are transmitted toward the concave surface 52, which reflects the beams to the localized area 30. Preferably, the localized area 30 is a focal point area 56. This causes a high concentration of heat at the focal point area 56, resulting in rapid air expansion, which generates a corresponding amount of acoustic energy. By controlling which lasers 38 are activated, alone or in combination, and by controlling the duration of time each laser 38 is active, a desired acoustic profile can be generated. The controller 24 selectively activates the lasers 38 to produce the predetermined amount of heat to form the phase-shifted acoustic profile that cancels or attenuates the variable noise profile. This will be discussed in greater detail below.

Figure 3:
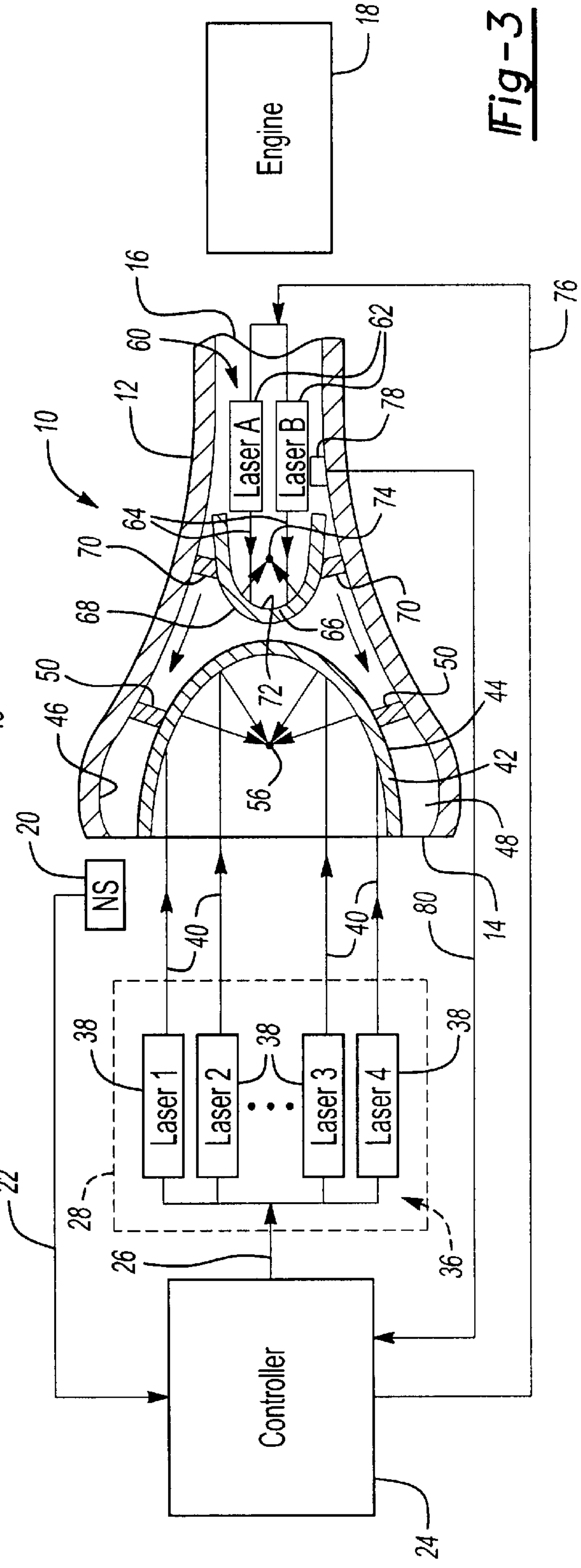
FIG. 3 is a schematic diagram of an alternate embodiment of the noise attenuation system.

In the embodiment shown in FIG. 3, the system includes the first laser array 36, which operates as explained above, and a second laser array 60. The second laser array 60 includes a plurality of lasers 62 that each transmits a laser beam 64 toward a curved surface. Preferably, a second curved member 66 is mounted within the air duct housing 12 facing the outlet 16. An exterior surface 68 of the curved member 66 is spaced apart from the interior surface 46 of the air duct housing 12 to form a portion of the annular passage 48 for air flow between the inlet 14 and engine intake. The curved member 66 is preferably attached to the air duct housing 12 with struts 70 or other similar members.

The curved member 66 defines a concave surface 72 that faces the second laser array 60. Any type of curved surface profile can be used, such as a parabolic surface, for example. The laser beams 64 are transmitted toward the concave surface 72, which reflects the beams 64 to a second localized area 74. Preferably, the localized area 74 is a focal point area that is located within the housing 12 between the second laser array 60 and the second curved member 66. This causes a high concentration of heat at the focal point area 74, resulting in rapid air expansion, which generates a corresponding amount of acoustic energy. The controller 24 generates a second control signal 76 to control the second laser array 60.

It should be understood that the noise detector sensor assembly 20 can include a single noise sensor or multiple noise sensors positioned throughout the air duct housing 12. Thus, a noise sensor component 78 can optionally be positioned adjacent to the second curved member 66 to measure noise and generate a corresponding noise signal 80, which is transmitted to the controller 24.

This is useful in a situation where both positive and negative noise pressure pulses are being generated. For example, if the noise that propagates through the system, as indicated by the arrows, has as negative pressure pulse profile then the first laser array 36 can be configured and activated accordingly to generate a positive pulse profile to cancel the negative pressure pulse profile. But, if the noise is reflected off another surface such as the first curved member 42, second curved member 66, or housing 12, then a portion of the noise can experience a phase change to form a positive pressure profile portion of the overall variable noise profile. The second laser array 60 can be configured and activated accordingly to generate a negative pulse profile to cancel the positive pressure profile portion. Thus, by selectively controlling which lasers 38 and 62 are activated, alone or in combination, and by selectively controlling the duration of time each laser 38 and 62 is active, a desired acoustic profile can be generated to attenuate or cancel the variable noise profile.

It should be understood that the embodiment shown in FIG. 2 with one laser array 36 can operate independently from the embodiment shown in FIG. 3, which utilizes first 36 and second 60 laser arrays. It should also be understood that any number of lasers 38 can be used in each of the arrays 36, 60 to produce the desired predetermined amount of heat at the desired focal point area. Preferably, more than one laser 38 is used to reduce possible injury to vehicle operators or passengers as a result of exposure to the laser beam. Further, any type of laser known in the art could be used including defocused lasers, however, laser-emitting diodes (LEDs) are preferred. The lasers 38 and 62 are mounted and arranged in an array to suit the vehicle application.

As discussed above, the controller 24 selectively activates the lasers 38, 62 to produce the predetermined amount of heat to form the phase-shifted acoustic profile that cancels or attenuates the variable noise profile. An example of how this is accomplished is shown in FIGS. 4–7.

Figure 4:
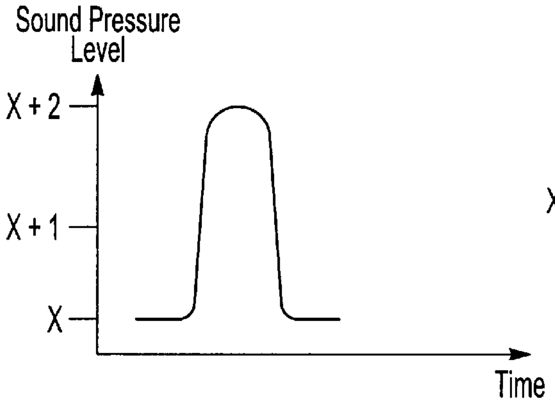
FIG. 4 is one example of a noise profile generated by the noise attenuation system incorporating the subject invention, represented on a Sound Pressure Level v. Time graph.

This example applies to the embodiment shown in FIG. 2, where the first laser array 36 includes four (4) lasers 38. Selection of the individual lasers 38 allows modulation of the acoustic profile. For example, if all four lasers 38 are on, then a noise comprising a sharp bang would be generated. This is shown in FIG. 4, which indicates a high sound pressure level (SPL).

Figure 5:
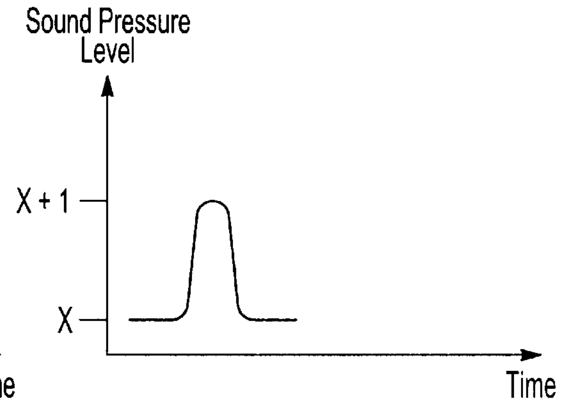
FIG. 5 is another example of a noise profile generated by the noise attenuation system incorporating the subject invention, represented on a Sound Pressure Level v. Time graph.

If only two or three lasers 38 are on, then a noise comprising a softer bang would be generated. This is shown in FIG. 5, which indicates a lower SPL then that shown in FIG. 4.

Figure 6:
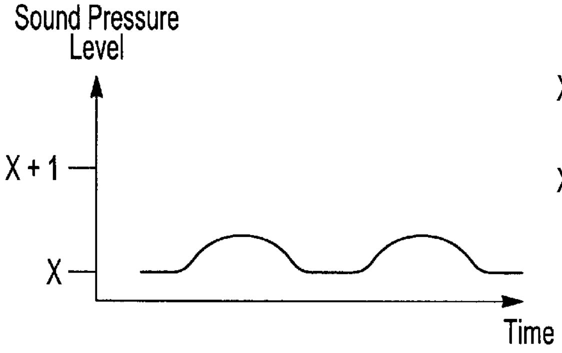
FIG. 6 is another example of a noise profile generated by the noise attenuation system incorporating the subject invention, represented on a Sound Pressure Level v. Time graph.

If the lasers 38 are pulsed, then controlled wave shaping can be used to generate a desired noise profile. This is shown in FIG. 6, which indicates a periodic wave noise SPL.

Figure 7:
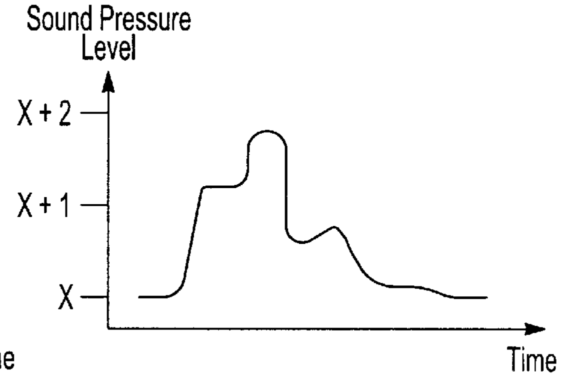
FIG. 7 is another example of a noise profile generated by the noise attenuation system incorporating the subject invention, represented on a Sound Pressure Level v. Time graph.

Finally, if a combination of pulsing and constant activation is used, then any type of shaped profile can be generated. This is shown in FIG. 7, which indicates a combination of a pulse, plus two lasers that are on, plus a second pulse. It should be understood that FIGS. 4–7 are merely one example of how a desired acoustic profile can be generated. An infinite number of acoustic profiles can be generated by monitoring engine noise and controlling laser activation and pulsing. The number of lasers, activation of lasers, and acoustic profile generation will vary from vehicle to vehicle.

Although a preferred embodiment of this invention has been disclosed, a worker of ordinary skill in this art would recognize that certain modifications would come within the scope of this invention. For that reason, the following claims should be studied to determine the true scope and content of this invention.

What is claimed is:

1. An active noise attenuation apparatus for an air induction system comprising:

an air duct housing having an inlet into which air is drawn and an outlet operably connected to an engine that propagates noise back through said air duct housing toward said inlet;

a heat generating mechanism for selectively producing a predetermined amount of heat within a localized area adjacent to said air duct housing, said predetermined amount of heat being sufficient to produce a desired acoustic energy as a result of rapid air expansion at said localized area; and a controller for sending a control signal to said heat generating mechanism to generate a desired acoustic profile to attenuate said noise by varying said predetermined amount of heat over time.

2. An apparatus according to claim 1 including a sound detector for sensing said noise emanating from said air duct housing, generating a noise signal corresponding to said noise, and communicating said noise signal to said controller.

3. An apparatus according to claim 2 wherein said noise varies over time to produce variable noise profile represented by said noise signal and wherein said controller generates said control signal based on said noise signal to produce said desired acoustic profile as a phase-shifted acoustic profile that cancels said variable noise profile.

4. An apparatus according to claim 3 wherein said localized area is positioned within said air duct housing adjacent to said inlet.

5. An apparatus according to claim 3 wherein said heat generating mechanism comprises an electrical spark generator that produces a plurality of electrical sparks within said localized area to form said phase-shifted acoustic profile.

6. An apparatus according to claim 3 wherein said heat generating mechanism comprises a first plurality of lasers arranged in an array wherein each of said first plurality of lasers selectively transmits a laser beam toward a first curved surface positioned within said air duct housing adjacent to said inlet and wherein said controller selectively activates said lasers to produce said predetermined amount of heat to form said phase-shifted acoustic profile.

7. An apparatus according to claim 6 including a first member mounted within said air duct housing to form said first curved surface wherein said first curved surface comprises a first concave surface facing outwardly from said inlet.

8. An apparatus according to claim 7 wherein said first concave surface comprises a parabolic surface.

9. An apparatus according to claim 7 including a second plurality of lasers wherein each of said second plurality of lasers selectively transmits a laser beam towards a second curved surface positioned within said air duct housing between said first member and said outlet and wherein said controller selectively activates said second plurality of lasers via said control signal to produce a second predetermined amount of heat at a second localized area within said air duct housing to form a second phase-shifted acoustic profile wherein a combination of said first and second phase-shifted profiles cancels said variable noise profile.

10. An apparatus according to claim 8 including a second member mounted within said air duct housing to form said second curved surface wherein said second curved surface comprises a second concave surface facing a direction opposite of said first concave surface.

11. An apparatus according to claim 10 wherein said second concave surface comprises a parabolic surface.

12. A method for attenuating noise in an air induction system comprising the steps of:

propagating noise through an air duct housing having an inlet into which air is drawn and an outlet operably connected to an engine;

generating a predetermined amount of heat within a localized area adjacent to the air duct housing that is sufficient to produce a desired acoustic energy as a result of rapid air expansion at the localized area; and varying the predetermined amount of heat over time to generate a desired acoustic profile to attenuate the noise.

13. A method according to claim 12 including the steps of sensing the noise propagated through the air duct housing, generating a noise signal corresponding to the noise, and varying the predetermined amount of heat in response to the noise signal.

14. A method according to claim 13 including the steps of varying the noise over time to produce variable noise profile represented by the noise signal and generating the desired acoustic profile as a phase-shifted acoustic profile that cancels the variable noise profile.

15. A method according to claim 14 including the steps of generating a plurality of electrical sparks to produce the phase-shifted acoustic profile.

16. A method according to claim 14 including the steps of transmitting a plurality of laser beams to a focal point area coinciding with the localized area to produce the phase-shifted acoustic profile.

17. A method according to claim 16 including the steps of positioning a curved surface within the air duct housing at the inlet, selectively activating and transmitting at least one of the laser beams toward the curved surface, and transmitting the at least one of the laser beams to the focal point area via the curved surface.

18. An active noise attenuation apparatus for an air induction system comprising:

an air duct housing having an inlet into which air is drawn and an outlet operably connected to an engine that propagates noise back through said air duct housing toward said inlet;

a sound detector for sensing said noise emanating from said air duct housing and generating a noise signal corresponding to said noise;

a first curved member mounted inside said air duct housing and circumferentially spaced apart from an interior surface of said air duct housing to form an annular air flow passage that interconnects said inlet and said outlet;

a first laser array including a plurality of lasers mounted in a predetermined external configuration relative to said air duct housing with each of said lasers selectively transmitting a laser beam toward said first curved member wherein said first curved member reflects said laser beams to a focal point area adjacent to said inlet to generate a predetermined about of heat; and a controller for determining which of said lasers should be activated in response to said noise signal and transmitting a control signal to said first laser array to selectively activate and deactivate said lasers over time to generate a desired acoustic profile to attenuate said noise.

19. An apparatus according to claim 18 wherein said noise varies over time to define a noise profile represented by said noise signal and wherein said controller varies said predetermined amount of heat over time to define a variable heat profile by modifying said control signal in response to noise variations tracked by said noise signal, said variable heat profile being sufficient to produce a phase-shifted acoustic profile that cancels said noise profile as a result of rapid air expansion at said focal point area.

20. An apparatus according to claim 19 including a second curved member mounted inside said air duct housing between said first curved member and said outlet and a second laser array including a plurality of lasers mounted in a predetermined internal configuration relative to said air duct housing with each of said lasers selectively transmitting a laser beam toward said second curved member in response to said control signal wherein said second curved member reflects said laser beams to a second focal point area to generate a second predetermined amount of heat to form a second phase-shifted acoustic profile wherein a combination of said first and second phase-shifted profiles cancels said noise profile.

* * * * *